United States Patent [19]

Au

[11] Patent Number: 4,797,418

[45] Date of Patent: Jan. 10, 1989

[54] ANTIBACTERIAL CYANOMETHYL CARBOXYLATES

[75] Inventor: Andrew T. Au, Needham, Mass.

[73] Assignee: The Dow Chemical Company, Midland, Mich.

[21] Appl. No.: 895,651

[22] Filed: Aug. 12, 1986

Related U.S. Application Data

[62] Division of Ser. No. 756,904, Jul. 19, 1985, Pat. No. 4,625,045.

[51] Int. Cl.$^4$ .............................................. A01N 37/34
[52] U.S. Cl. ..................................... 514/521; 514/527
[58] Field of Search ................................. 514/521, 527

[56] References Cited

U.S. PATENT DOCUMENTS

| | | | |
|---|---|---|---|
| 3,758,526 | 9/1973 | Fujita et al. | 260/404 |
| 3,873,591 | 3/1975 | Smith et al. | 260/456 |
| 4,115,430 | 9/1978 | Rohr | 260/465 |
| 4,123,451 | 10/1978 | Sheldon et al. | 260/465 |
| 4,252,814 | 2/1981 | Wepplo et al. | 424/266 |

FOREIGN PATENT DOCUMENTS 0093338  4/1983  European Pat. Off. .

OTHER PUBLICATIONS

Chemical Abstracts 62:5158d.
(1976) Chemical Abstracts 86:16157t.

*Primary Examiner*—Allen J. Robinson
*Attorney, Agent, or Firm*—Craig E. Mixan; Ronald G. Brookens

[57] ABSTRACT

A one step process for the preparation of certain cyanomethyl carboxylates is disclosed which comprises reacting an appropriate acyl compound with a water soluble metal cyanide such as sodium cyanide or potassium cyanide and an aldehyde such as formaldehyde, acetaldehyde, or benzaldehyde. Also disclosed is a method for inhibiting bacteria by contacting said bacteria or habitat thereof with an effective amount of an antibacterial cyanomethyl carboxylate.

2 Claims, No Drawings

ANTIBACTERIAL CYANOMETHYL CARBOXYLATES

CROSS-REFERENCE TO RELATED APPLICATION

This application is a divisional of Applicant's copending application Ser. No. 756,904, filed on July 19, 1985, which application issued as U.S. Pat. No. 4,625,045 on Nov. 25, 1986.

BACKGROUND OF THE INVENTION

This invention relates to a novel one step process for the preparation of certain cyanomethyl carboxylates. Many of the carboxylates prepared by the process of the present invention are known to have certain insecticidal/acaricidal activities and/or are intermediates for the preparation of other useful compounds (e.g., see European Patent Application No. 93,338 A). Known methods for preparation of compounds similar to those described in the present invention require several steps and/or the use of an unstable intermediate such as glycolonitrile (e.g., see U.S. Pat. No. 3,873,591). The process of the present invention is simple, efficient and a significant improvement over methods taught in the prior art.

The invention also relates to a method for inhibiting bacteria by contacting said bacteria or habitat thereof with certain carboxylates prepared by the process of the present invention.

SUMMARY OF THE INVENTION

This invention relates to a novel process for preparing compounds of the formula:

wherein R represents:
(a) —CCl$_3$;
(b) —CF$_3$;
(c) —CH$_2$NO$_2$;
(d) —CH$_2$CN;
(e) —CH$_2$N$^\oplus$(R$^2$)$_3$;
  wherein each R$^2$ is independently alkyl or aryl;
(f)

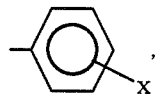

wherein X is one to three election-withdrawing groups;
and R$^1$ represents H, alkyl or aryl;
which comprises
reacting an acyl compound of the formula:

wherein R is defined hereinabove and T represents:
(a) halo,
(b) —CN,
(c)

wherein R$^3$ is alkyl or aryl; with an aldehyde and a water soluble metal cyanide, said process occurring in a solvent system under conditions at which the compound of formula I is formed.

As used herein, the term "alkyl" refers to an aliphatic straight, branched or cyclic alkyl moiety of from one to ten carbon atoms, inclusive; the term "halo" refers to a member selected from the group consisting of chloro, bromo, and fluoro; and the term "aryl" refers to aromatic moieties such as phenyl, naphthyl, and the like.

The present invention also relates to a method for inhibiting bacteria which comprises contacting said bacteria or habitat thereof with an effective amount of an antibacterial compound of formula I.

DETAILED DESCRIPTION OF THE INVENTION

To prepare the compound of formula I the molar ratio of the reactants, i.e., acyl compound of formula II: aldehyde:metal cyanide is typically between about 0.5:1:0.5 and about 10:1:10, respectively, with about 1:1:2, respectively, being preferred.

Suitable aldehydes for use as a reactant in the process of the present invention are those aldehydes which result in the desired R$^1$ moiety of the compound of formula I. For example, when the aldehyde is formaldehyde the desired product is a cyanomethyl carboxylate, when the aldehyde is actaldehyde the desired product is an α-methyl cyanomethyl carboxylate, and when the aldehyde is benzaldehyde the desired product is an α-phenyl cyanomethyl carboxylate.

The metal cyanide for use in the process of the present invention can be any water soluble metal cyanide such as KCN, NaCN, and the like.

The election-withdrawing groups (designated hereinabove as "X") which can be substituted on the phenyl ring of the compound of formula I or the compound of formula II can be, for example: halo; —NO$_2$; —SO$_2$R$^4$, wherein R$^4$ is alkyl or aryl; —CCl$_3$; —CF$_3$; —N$^\oplus$(R$^5$)$_3$, wherein each R$^5$ is alkyl;

wherein R$^6$ is alkyl or aryl; and the like.

The process of the present invention can be carried out in a monophasic solvent system using one or more polar solvents such as dimethylsulfoxide, dimethylformamide, tetrahydrofuran, hexamethylphosphoric triamide, glycol methyl ethers, and the like. However, the process of this invention is preferably carried out in a biphasic solvent system comprising water and at least one water immiscible organic solvent such as chloroform, methylene chloride, carbon tetrachloride, toluene, benzene, ethyl ether, and the like.

The process of the present invention typically proceeds at a temperature in the range of about −20° to about 100° C. with about 0° to about 40° C. being preferred. The reaction time is not critical, but typically the desired product will be formed in sufficient quantity in about one hour or less after addition of all reactants.

However, additional time may be desired depending upon the other reaction conditions.

After the compound of formula I is formed in the reaction mixture, said compound can be isolated, extracted and purified by using standard procedures known in the art.

The present invention is also directed to a method for inhibiting bacteria by contacting said bacteria or habitat thereof with an effective amount of an antibacterial compound of formula I. The antibacterial compounds described in the present invention can be used in a wide variety of applications where inhibition of bacteria is desired. The antibacterial compounds of formula I can be used either alone or in combination with acceptable carriers, commonly used in the art. One or more of antibacterial compounds of formula I or combinations containing the same and a carrier can be used as disinfectants, for example, to disinfect objects and instruments. As used herein, the term "antibacterial compounds" refers to those compounds of formula I which inhibit bacteria; the term "inhibit", "inhibition" or "inhibiting" refers to supression, control or kill of bacteria; and the term "effective amount" refers to that amount of one or more antibacterial compounds of formula I which inhibits bacteria.

The present invention is further illustrated by the following examples; however, these examples should not be interpreted as a limitation upon the scope of the present invention.

EXAMPLE 1

Preparation of Cyanomethyl-p-Nitrobenzoate

To a mixture of 10 milliliters (ml) of 37 percent formaldehyde in water and 9.3 grams (g) of p-nitrobenzoyl chloride in 20 ml of methylene chloride at 0° C., was added 7.5 g of sodium cyanide in 20 ml of water at a rate such that the temperature was kept at about less than 10° C. After the addition was complete, the mixture was stirred at 0° C. for another hour, then poured onto ice and ether added which resulted in an aqueous layer and an organic layer. The organic layer containing ether was then separated from the aqueous layer. The organic layer was then washed with saturated sodium bicarbonate, dried over magnesium sulfate and concentrated which gave a colorless oil which solidified upon standing at ambient temperature. The yield of solid was 7.2 g, melting point (m.p.) 74°–80° C. The solid was then recrystallized in isopropanol which yielded 5.2 g of a colorless, needlelike solid, m.p. 80°–82° C. The solid was confirmed to be cyanomethyl-p-nitrobenzoate by infrared and nuclear magnetic resonance analyses.

EXAMPLE 2

Using standard procedures known in the art, cyanomethyl-p-nitrobenzoate at a concentration of 500 parts per million was found to inhibit growth of the following bacteria: *Erwinia amylovora, Fusobacterium necrophorum, Staphylococcus aureus, Escherichia coli,* and *Proteus mirabilis.*

I claim:

1. A method for inhibiting bacteria which comprises contacting said bacteria with a bacteria inhibiting amount of an antibacterial compound of the formula

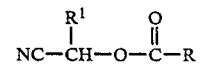

wherein R represents:
(a) —CCl$_3$;
(b) —CF$_3$;
(c) —CH$_2$NO$_2$;
(d) —CH$_2$CN;
(e) —CH$_2$⊕N(R$^2$)$_3$;
wherein each R$^2$ is independently alkyl or aryl; or
(f)

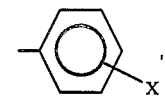

wherein X is one to three election-withdrawing groups;
and R$^1$ represents H, alkyl or aryl.

2. The method of claim 1 wherein said antibacterial compound is cyanomethyl p-nitrobenzoate.

* * * * *